United States Patent
Galis et al.

[11] Patent Number: 6,099,223
[45] Date of Patent: Aug. 8, 2000

[54] ADJUSTABLE WEDGE WASHER

[75] Inventors: Erik J. Galis, Cranberry Township; Robert S. Whitelaw, III, Grove City; Scott L. Maxwell, Slippery Rock, all of Pa.

[73] Assignee: Instron Corporation, Canton, Mass.

[21] Appl. No.: 09/216,790

[22] Filed: Dec. 21, 1998

[51] Int. Cl.[7] .................................................. F16B 43/02
[52] U.S. Cl. ........................... 411/538; 411/275; 411/936
[58] Field of Search ................................... 411/538, 537, 411/274, 275, 230, 936; 73/761

[56] References Cited

U.S. PATENT DOCUMENTS

| | | | |
|---|---|---|---|
| 3,285,568 | 11/1966 | Biach | 411/538 |
| 4,177,999 | 12/1979 | Raber | 411/537 |
| 4,559,830 | 12/1985 | Plummer | 73/761 |

FOREIGN PATENT DOCUMENTS

| | | | |
|---|---|---|---|
| 581645 | 12/1924 | France | 411/537 |
| 1092487 | 4/1955 | France | 411/538 |
| 111778 | 12/1917 | United Kingdom | 411/371 |

*Primary Examiner*—Flemming Saether
*Attorney, Agent, or Firm*—Mark R. Galis; John E. Hyatt

[57] ABSTRACT

The subject invention relates to an adjustable wedge washer to be used in connection with various material testing machines which are used to mechanically test the strength of bolts, screws and other types of fasteners. The subject adjustable wedge washer includes two wedge washers being joined together mechanically with a snap ring so that they are not separable. The wedge washers then rotate relative to each other to form a variable testing angle relative to the fastener.

9 Claims, 1 Drawing Sheet

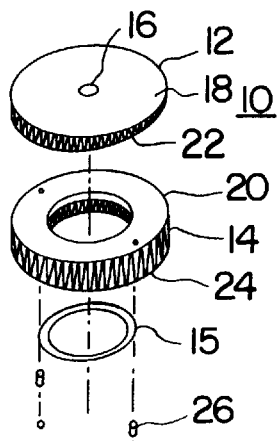 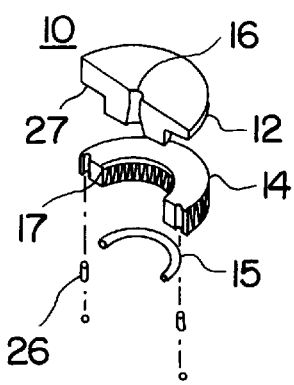
FIG. 1    FIG. 2
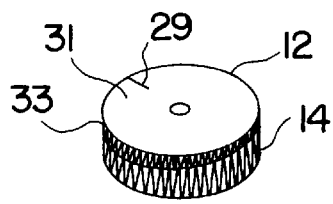 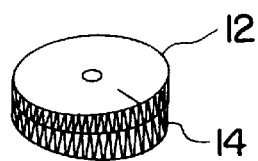
FIG. 3A    FIG. 3B
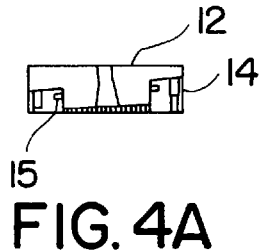 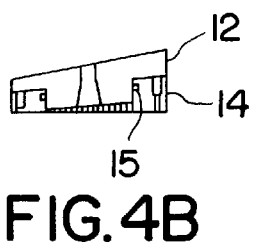
FIG. 4A    FIG. 4B
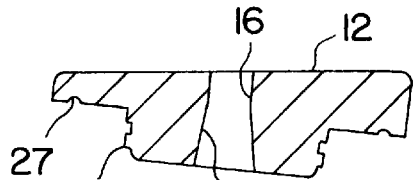 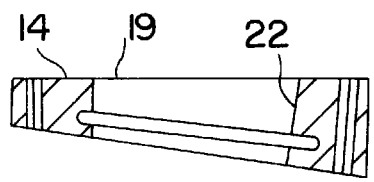
FIG. 5    FIG. 6
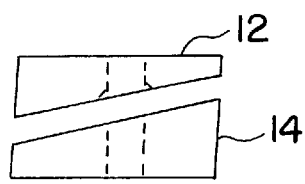 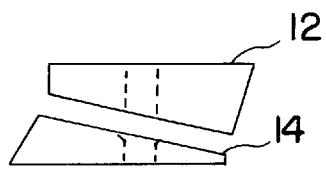
FIG. 7A    FIG. 7B

ADJUSTABLE WEDGE WASHER

FIELD OF THE INVENTION

The present invention relates to an adjustable wedge washer to be used in connection with various material testing machines which are used to mechanically test the strength of bolts, screws and other types of fasteners. The current method for testing such fasteners is to place a flat washer under the head of the bolt, screw or other fastener to be tested to conduct what is well known in the material testing industry as a "proof test." After the proof test is completed, the bolt, screw or other fastener is removed from the fixture of the testing machine. The flat washer is then removed from the bolt or screw and replaced with a separate wedge washer (i.e. a washer having an angled top surface relative to its bottom surface). The bolt, screw or other fastener is then put back in the fixture of the testing machine and the fastener is tested to failure. The aforementioned testing method requires disassembly of the test fixture and removal of the fastener so the washer can be changed from a flat washer to a wedge washer. This method is time consuming since after each test such a disassembly and replacement has to occur. The subject invention improves on the current testing method since a single washer, i.e. the subject adjustable wedge washer, is used for both the flat and wedge washer portions of the test. The subject invention allows for much more efficient testing since the bolt, screw or other fastener does not have to be removed from the fixture of the testing machine after the flat washer test and prior to the wedge washer test.

SUMMARY OF THE INVENTION

According to the invention, there is provided an adjustable wedge washer for use in conducting material testing. The angle of the top surface of the adjustable wedge washer relative to the fastener to be tested can be changed from zero degrees to some pre-determined maximum angle. The subject adjustable wedge washer is composed of two wedge washers, each of a predetermined angle. The two wedge washers are placed on top of one another to form a unitary washer structure to be placed on the bolt, screw or other fastener to be tested. By varying the orientation of one wedge washer relative to the other, a wedge angle from zero to a predetermined maximum is achieved.

In one embodiment of the invention, the adjustable wedge washer is composed of two wedge washers which can be separated and mechanically rotated relative to each other to form either a zero degree angle or the maximum wedge angle. During testing, the two wedge washers are positioned together on the bolt and the proper testing angle can be maintained by the use of locator pins and detents. Alignment of the two wedge washers to create the proper testing angle can further be achieved through the use of locator lines on the two wedge washers.

Another embodiment of the adjustable wedge washer involves the two wedge washers being joined together mechanically with a snap ring of a type commonly known in the art so they are not separable. One of the two wedge washers can have spring loaded plungers which lock in place in detents located on the opposed surface of the other wedge washer. Each detent would correspond to a specific angle relative to the fastener. This design ensures the mated wedges stay together. This design allows for the two wedges to easily rotate relative to each other to form the testing angles described above and so the testing angle can easily be varied from test to test.

Further, another improvement in the subject invention, the wedge washers can be combined with an automated rotating mechanism, such as a pneumatic piston, to allow for the wedge washer angle to be varied automatically without human involvement thus improving test efficiency even further.

BRIEF DESCRIPTION OF THE DRAWINGS

FIG. 1 is an exploded perspective view of the adjustable wedge washer assembly.

FIG. 2 is an exploded perspective and cut-away view of the adjustable wedge washer assembly of FIG. 1.

FIGS. 3A and 3B are, respectively, assembled perspective views of the wedge washer assembly at a zero (flat) angle and at a maximum angle.

FIGS. 4A and 4B are cut away views of FIGS. 3A and 3B, respectively.

FIG. 5 is a cross section view of the top wedge washer to show the opening for the associated bolt.

FIG. 6 is a cross section view of the bottom wedge washer to show the opening for the associated bolt.

FIGS. 7A and 7B are sketches depicting two varied abutting relations of the wedge washer surfaces.

DETAILED DESCRIPTION OF THE INVENTION

Referring now to FIG. 1 in greater detail, there is illustrated an exploded perspective view of an adjustable wedge washer 10 constructed according to the teachings of the present invention. As noted above, FIG. 2 is an exploded perspective cut-away view of FIG. 1. As shown in a preferred embodiment, the adjustable wedge washer 10 includes a top wedge washer 12 and a bottom wedge washer 14 which are interconnected such as by a snap ring 15 which is positioned in recess 17 of bottom washer 14 and a groove in washer 12, see also FIGS. 4A and 4B which shows the subject invention at a zero degree angle and at the maximum angle. The top wedge washer 12 contains an opening 16 in which a bolt, screw or other fastening device (not shown) can be inserted for placement into the fixture of a standard material testing machine, as is well known in the art. As more closely seen from FIGS. 5 and 6, the opening 16 for the top wedge washer 12 is formed to include a tapered interior surface 27. Wedge washer 12 includes a downwardly depending portion 21 which is received by an opening 19 in the bottom wedge washer 14. Wedge washer 14 is formed to have the interior surface 22 of opening 19 to be perpendicular to the bottom surface of the wedge washer 14.

The adjustable wedge washer 10 can be composed of two wedge washers 12 and 14 of maximum five degree angles, or any other suitable wedge angle. As shown in FIGS. 4 and 7, the wedge washers 12 and 14 can be oriented such that the total angle is zero degrees (FIG. 7A), or the five degree wedge washers 12 and 14 can be rotated ½ turn to form a ten degree wedge. As shown in FIG. 2 the two wedge washers 12 and 14 are positioned relative to one another with locator pins or ball plungers 26 and associated detents 27, or by locator lines 29 formed on the outer surface 31, to maintain one of the specific angles desired. Locator lines can also be conveniently positioned on the edge surfaces 33 of the mating wedge washers 12 and 14. Further, the wedge washers 12 and 14 can be combined with an automated rotating mechanism such as a pneumatic piston to allow for the washer angle to be varied automatically without human involvement, thus improving testing efficiency.

In a more basic version of the invention, the two wedge washers 12 and 14 (FIG. 7B) can be separated and rotated to form either a zero degree or other degree wedge angles.

It should be noted that modification to the subject invention may be made by those in the art without departing from the teachings of the subject invention. Accordingly, the scope of the invention is only to be limited as necessitated by the accompanying claims.

We claim:

1. An adjustable wedge washer comprising:
   a) at least two wedge washers;
   b) each of said wedge washers including an angled surface angled 5 degrees relative to a common plane;
   c) means for moveably linking said wedge washers and positioning the angled surface of one wedge washer to abut the angled surface of the other wedge washer; and wherein
   d) said wedge washers are rotatable relative to one another to define a top surface angle which can be varied from a zero degree angle to a maximum angle by rotating the wedge washers relative to the one and the other.

2. A proof test device comprising:

a first wedge having a first angled surface angled relative to a common plane and defining an opening;

a second wedge having a top surface angled relative to said common plane defining a wedge angle, a second angled surface, and including a depending portion depending from the second angled surface, wherein the depending portion is rotatable positioned in the first wedge opening, wherein the second angled surface is rotatably positioned relative to the first angled surface, and wherein the wedge angle is varied between zero and at least 5 degrees relative to said common plane by rotating the second angled surface relative to the first angled surface.

3. The proof test device of claim 2, wherein the first wedge opening includes a ring postioned therein and the depending portion includes a groove engaging the ring.

4. The proof test device of claim 3, wherein the first and second wedges are wedge washers.

5. The proof test device of claim 2, wherein the first wedge is mechanically joined to the second wedge via a groove in the second wedge and a protrusion extending from the first wedge.

6. The proof test device of claim 2, wherein the first wedge is rotatably interconnected to the second wedge via a ring recessed in the first wedge opening and a groove in the depending portion.

7. The proof test device of claim 6, wherein the second wedge top surface defines a tapered opening for receiving a fastener to be proof tested.

8. The proof test device of claim 2, wherein the second wedge top surface defines an opening for receiving a fastener to be proof tested, and a protrusion extending from and transverse to the downwardly depending portion, and wherein the first wedge opening includes a recess for receiving the protrusion.

9. The proof test device of claim 8, wherein the protrusion is a ring.

* * * * *